(12) United States Patent
Miller et al.

(10) Patent No.: US 6,765,005 B2
(45) Date of Patent: Jul. 20, 2004

(54) FAB I INHIBITORS

(75) Inventors: William H. Miller, Collegeville, PA (US); Kenneth A. Newlander, West Chester, PA (US); Mark A. Seefeld, Collegeville, PA (US)

(73) Assignee: Affinium Pharmaceuticals, Inc., Toronto (CA)

( * ) Notice: Subject to any disclaimer, the term of this patent is extended or adjusted under 35 U.S.C. 154(b) by 0 days.

(21) Appl. No.: 10/292,687

(22) Filed: Nov. 12, 2002

(65) Prior Publication Data

US 2003/0139377 A1 Jul. 24, 2003

Related U.S. Application Data

(63) Continuation of application No. 09/959,172, filed as application No. PCT/US00/10695 on Apr. 19, 2000, now Pat. No. 6,503,903.
(60) Provisional application No. 60/130,101, filed on Apr. 20, 1999, and provisional application No. 60/129,928, filed on Apr. 19, 1999.

(51) Int. Cl.$^7$ ................. C07D 243/14; C07D 403/12; C07D 405/12; C07D 417/12; A61K 31/5513
(52) U.S. Cl. ..................... 514/221; 540/510
(58) Field of Search ............... 514/221; 540/510

(56) References Cited

U.S. PATENT DOCUMENTS

| | | | |
|---|---|---|---|
| 3,828,068 A | 8/1974 | Minieri | 260/310 C |
| 4,154,943 A | 5/1979 | Kuehne | 514/51 |
| 4,977,159 A | 12/1990 | Sevrin et al. | 514/292 |
| 5,614,551 A | 3/1997 | Dick et al. | 514/454 |
| 5,624,941 A | 4/1997 | Barth et al. | 514/326 |
| 5,932,743 A | 8/1999 | Collini et al. | 548/508 |
| 5,985,867 A | 11/1999 | Rodgers et al. | 514/218 |
| 6,346,391 B1 | 2/2002 | Oethinger et al. | 435/32 |
| 6,372,752 B1 | 4/2002 | Staveski et al. | 514/273 |
| 6,451,816 B1 | 9/2002 | Biedermann et al. | 514/318 |
| 6,469,046 B1 | 10/2002 | Daines et al. | 514/419 |
| 6,503,903 B1 | 1/2003 | Miller et al. | 514/221 |
| 6,503,908 B1 | 1/2003 | Maw | 514/243 |
| 6,559,172 B1 | 5/2003 | Heerding et al. | 514/396 |
| 6,573,272 B1 | 6/2003 | Miller et al. | 514/392 |

FOREIGN PATENT DOCUMENTS

| | | |
|---|---|---|
| WO | WO 95/18619 | 7/1995 |
| WO | WO 96/00730 | 1/1996 |
| WO | WO 97/48696 | 12/1997 |
| WO | WO 98/57952 | 12/1998 |
| WO | WO 01/26652 | 4/2001 |
| WO | WO 01/26654 A1 | 4/2001 |
| WO | WO 01/27103 A1 | 4/2001 |
| WO | WO 01/48248 | 7/2001 |
| WO | WO 02/42273 | 5/2002 |
| WO | WO 02/48097 | 6/2002 |

OTHER PUBLICATIONS

Abou–Gharbia et al., "Psychotropic Agents: Synthesis and Antipysychotic Activity of Substituted B–Carbolines," J. Med. Chem., 30(6): 1100–1115 (1987).

Ahsan et al., "Reserpine Anlogues: Synthesis of B–Carboline Derivatives," J. Chem. Soc., pp. 3928–3920 (1963).

Database Crossfire Beilstein, 1966, Database accession No. 2819049, 2819050, XP002216033.

Database CA on STN, AN 7:66733, Rosenmund et al., "Chemistry of indole II . . . ," Chem Ber. 103(2): 496–509 (1970).

Database CAOLD on STD, AN CA51:10524d, Hellman et al., "N–Mannich bases (VI) condensation . . . ," Direct Submission (1953).

Database CAPLUS on STN, An 1977:439214. Misztal et al., "Synthesis and pharmacologic properties of pyridoyl . . . ," Arch Immuno Ther Exp. 24(6): 851–862 (1976).

Himmer et al., "Synthesis and Antibacterial in Vitro Activity of Novel Analogues of Nematophin," Bioorganic & Medicinal Chemistry Letters, 8(15): 2045–2050 (Aug. 1998).

Jianxiong et al., "Synthesis and Antistaphylococcal Activity of Nematophin and Its Analogs," Bioorganic & Medicinal Chemistry Letters, Oxford, GB, 7(10): 1349–1352, (May 20, 1977) XP004136332.

Miller et al., Discovery of Aminopyridine–Based Inhibitors of Bacterial Enoyl–ACP Reductase (FABI); J. Med. Chem. 2002, vol. 45, pp. 3246–3256.

Misztal et al., "Synthesis and Pharmacologic Properties of Pyridol Derivatives of 3–Methylaminoindole 2–Methyltryptamine and Isotryptamine," Archivum Immnologiae et Therapiae Experimentalis, 24(6): 851–852 (1976).

Pachter et al., "The Chemistry of Hortiamine and 6–Methoxyhetsinine," J. Amer. Chem., 83:635–642 (1961).

Rehse et al., "Dopaminanaloge 1,2,3,4–Tetrahydro–B–Carboline," Arch. Pharm., 311(1):11–18 (1978).

Shoji et al., "Two Novel Alkaloids from Evodia Rutaecarpa," J. Natural Products, 52(5):1160–1162 (1989).

Primary Examiner—Bruck Kifle
(74) Attorney, Agent, or Firm—Foley Hoag, LLP

(57) ABSTRACT

Compounds of the formula (I) are disclosed which are Fab I inhibitors and are useful in the treatment bacterial infections:

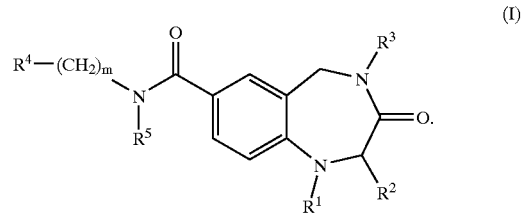

(I)

10 Claims, No Drawings

FAB I INHIBITORS

This is a continuation/divisional of application Ser. No. 09/959,172 filed Oct. 18, 2001, now U.S. Pat. No. 6,503,903 which is a 371 of International Application No. PCT/US00/10695, which claims priority to U.S. Provisional application No. 60/130,101 filed Apr. 20, 1999 and 60/129,928 filed Apr. 19, 1999.

FIELD OF THE INVENTION

This invention relates to pharmaceutically active compounds which inhibit Fab I and are useful for the treatment of bacterial infections.

BACKGROUND OF THE INVENTION

While the overall pathway of saturated fatty acid biosynthesis is similar in all organisms, the fatty acid synthase (FAS) systems vary considerably with respect to their structural organization. Vertebrates and yeast possess a FAS in which all the enzymatic activities are encoded on one or two polypeptide chains, respectively, and the acyl carrier protein (ACP) is an integral part of the complex. In contrast, in bacterial FAS, each of the reactions is catalyzed by a distinct, mono-functional enzyme and the ACP is a discrete protein. Therefore, there is considerable potential for the selective inhibition of the bacterial system by antibacterial agents.

Fab I (previously designated EnvM) functions as an enoyl-ACP reductase (Bergler, et al, (1994), *J. Biol. Chem.* 269, 5493–5496) in the final step of the four reactions involved in each cycle of bacterial fatty acid biosynthesis. In this pathway, the first step is catalyzed by β-ketoacyl-ACP synthase, which condenses malonyl-ACP with acetyl-CoA (FabH, synthase III). In subsequent rounds, malonyl-ACP is condensed with the growing-chain acyl-ACP (FabB and FabF, synthases I and II, respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP, which in turn is converted to acyl-ACP by NADH-dependent enoyl-ACP reductase (Fab I). Further rounds of this cycle, adding two carbon atoms per cycle, eventually lead to palmitoyl-ACP (16C), where upon the cycle is stopped largely due to feedback inhibition of Fab I by palmitoyl-ACP (Heath, et al, (1996), *J. Biol. Chem.* 271, 1833–1836). Thus, Fab I is a major biosynthetic enzyme and is a key regulatory point in the overall synthetic pathway of bacterial fatty acid biosynthesis. Therefore, Fab I is an ideal target for antibacterial intervention.

Studies have shown that diazaborine antibiotics inhibit fatty acid, phospholipid and lipopolysaccharide (LPS) biosynthesis and that the antibacterial target of these compounds is Fab I. For example, derivative 2b18 from Grassberger, et al (1984) *J. Med Chem* 27 947–953 has been reported to be a non-competitive inhibitor of Fab I (Bergler, et al, (1994), *J. Biol. Chem.* 269, 5493–5496). Also, plasmids containing the Fab I gene from diazaborine resistant *S. typhimurium* conferred diazaborine resistance in *E. coli* (Turnowsky, et al, (1989), *J. Bacteriol.*, 171, 6555–6565). Furthermore, inhibition of Fab I either by diazaborine or by raising the temperature in a Fab I temperature sensitive mutant is lethal. These results demonstrate that Fab I is essential to the survival of the organism (Bergier, et al, (1994), *J. Biol. Chem.* 269, 5493–5496).

Recent studies have shown that Fab I is also the target for the broad spectrum antibacterial agent triclosan (McMurry, et al, (1998) *Nature* 394, 531–532). A crystal structure of the *E. Coli* Fab I complexed with NAD and triclosan shows that triclosan acts as a site-directed, very potent inhibitor of Fab I by mimicking its natural substrate (Levy, et al, (1999) *Nature* 398, 383–384). Ward, et al ((1999) *Biochem.* 38, 12514–12525) have shown that there is no evidence for the formation of a covalent complex between Fab I and triclosan, which would be analogous to the diazaborines; triclosan differs from these compounds in that it is a reversible inhibitor of Fab I. The structural data for the complex of Fab I with NAD and triclosan provides important information about Fab I as a therapeutic target.

Importantly, it has now been discovered that certain compounds are Fab I inhibitors and have antibacterial activity, and, therefore, may be useful for the treatment of bacterial infections in mammals, particularly in man.

SUMMARY OF THE INVENTION

This invention comprises compounds of the formula (I), as described hereinafter, which inhibit Fab I and are useful in the treatment of bacterial infections.

This invention is also a pharmaceutical composition comprising a compound according to formula (I) and a pharmaceutically acceptable carrier.

This invention is also a method of treating bacterial infections by inhibiting Fab I. In a particular aspect, the compounds of this invention are useful as antibacterial agents.

DETAILED DESCRIPTION

This invention comprises compounds of formula (I):

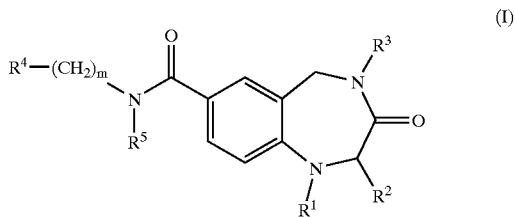

wherein:

$R^1$ is H, $C_{1-6}$alkyl or Ar—$C_{0-6}$alkyl;

$R^2$ is H, $C_{1-6}$alkyl, Ar—$C_{0-6}$alkyl, HO—$(CH_2)_n$— or R'OC(O)—$(CH_2)_n$—;

$R^3$ is A—$C_{0-4}$alkyl, A—$C_{2-4}$alkenyl, A—$C_{2-4}$alkynyl, A—$C_{3-4}$oxoalkenyl, A—$C_{3-4}$oxoalkynyl, A—$C_{1-4}$aminoalkyl, A—$C_{3-4}$aminoalkenyl, A—$C_{3-4}$aminoalkynyl, optionally substituted by any accessible combination of one or more of $R^{10}$ or $R^7$;

$R^4$ is

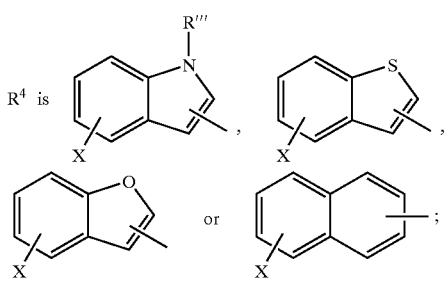

$R^5$ is H, $C_{1-6}$alkyl, Ar—$C_{0-6}$alkyl or $C_{3-6}$cycloalkyl-$C_{0-6}$alkyl;

A is H, $C_{3-6}$cycloalkyl, Het or Ar;

$R^7$ is —$COR^8$, —$COCR'_2R^9$, —$C(S)R^8$, —$S(O)_kOR'$, —$S(O)_kNR'R''$, —$PO(OR')$, —$PO(OR')_2$, —$B(OR')_2$, —$NO_2$, or tetrazolyl;

$R^8$ is —OR', —NR'R", —NR'SO$_2$R', —NR'OR', or —OCR'$_2$CO(O)R';

$R^9$ is —OR', —CN, —S(O)$_r$R', —S(O)$_k$NR'$_2$, —C(O)R', C(O)NR'$_2$, or —CO$_2$R';

$R^{10}$ is H, halo, —OR$^{11}$, —CN, —NR'R$^{11}$, —NO$_2$, —CF$_3$, CF$_3$S(O)$_r$—, —CO$_2$R', —CONR'$_2$, A—C$_{0-6}$alkyl-, A—C$_{1-6}$oxoalkyl-, A—C$_{2-6}$alkenyl-, A—C$_{2-6}$alkynyl-, A—C$_{0-6}$lkyloxy-, A—C$_{0-6}$alkylamino- or A—C$_{0-6}$alkyl-S(O)$_r$—;

$R^{11}$ is R', —C(O)R', —C(O)NR'$_2$, —C(O)OR', —S(O)$_k$R', or —S(O)$_k$NR'$_2$;

R' is H, C$_{1-6}$alkyl, Ar—C$_{0-6}$alkyl or C$_{3-6}$cycloalkyl-C$_{0-6}$alkyl;

R" is R', —C(O)R' or —C(O)OR';

R'" is H, C$_{1-6}$alkyl, Ar—C$_{0-6}$alkyl, HO—(CH$_2$)$_2$—, R'C(O)—, (R')$_2$NC(O)CH$_2$— or R'S(O)$_2$—;

X is H, C$_{1-4}$alkyl, OR', SR', C$_{1-4}$alkylsulfonyl, C$_{1-4}$alkylsulfoxyl, —CN, N(R')$_2$, CH$_2$N(R')$_2$, —NO$_2$, —CF$_3$, —CO$_2$R', —CON(R')$_2$, —COR', —NR'C(O)R', F, Cl, Br, I, or CF$_3$S(O)$_r$—;

k is 1 or 2;
m is 1, 2 or 3;
n is 1 to 6; and
r is 0, 1 or 2;

or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique racemic compound, as well as each unique nonracemic compound. These compounds may be synthesized and resolved by conventional techniques. In the formula (I) compounds of the present invention, the (R)-configuration at the 2-position of the 1,4-benzodiazepine ring system is preferred.

In cases in which compounds have unsaturated carbon-carbon double bonds, both the cis (Z) and trans (E) isomers are within the scope of this invention. In cases wherein compounds may exist in tautomeric forms, such as keto-enol tautomers, such as

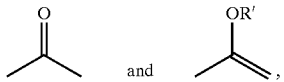

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in vivo.

The compounds of formula (I) inhibit Fab I. Inhibition of this enzyme is useful in the treatment of bacterial infections. Also, the compounds of this invention may be useful as antifungal agents. Additionally, the compounds may be useful in combination with known antibiotics.

With respect to formula (I):
Suitably, $R^4$ is

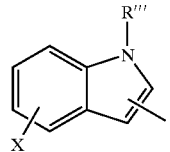

in which R'" is H, C$_{1-4}$alkyl or Ar—C$_{0-4}$alkyl and X is H, C$_{1-4}$alkyl, OR', SR', —CN, —CF$_3$, —CO$_2$R', F, Cl, Br or I.

Suitably, $R^3$ is H, C$_{1-6}$alkyl, Ar—C$_{0-6}$alkyl, Het-C$_{0-6}$alkyl, C$_{3-6}$cycloalkyl-C$_{0-6}$alkyl, —CH$_2$CF$_3$, —(CH$_2$)$_{1-2}$C(O)OR', or —(CH$_2$)$_2$OR', wherein R' is H or C$_{1-4}$alkyl. Preferably, $R^3$ is H, C$_{1-4}$alkyl or Ph-C$_{0-4}$alkyl.

Suitably, $R^1$ is H and m is 1.
Suitably, $R^5$ is H or C$_{1-4}$alkyl.
Suitably, $R^2$ is H, C$_{1-4}$alkyl, Ph-C$_{0-4}$alkyl, HO—(CH$_2$)$_{1-2}$— or R'OC(O)—(CH$_2$)$_{1-2}$—, wherein R' is H or C$_{1-4}$alkyl.

Representative of the novel compounds of this invention are the following:

(2S)-2-[(carbomethoxy)methyl]-N,4-dimethyl-N-[(1-methyl-1H-indol-2-yl)methyl]-3-oxo-2,3,4,5-tetrahydro-1H-1,4-benzodiazepine-7-carboxamide;

(2R)-2-[(carbomethoxy)methyl]-N,4-dimethyl-N-[(1-methyl-1H-indol-2-yl)methyl]-3-oxo-2,3,4,5-tetrahydro-1H-1,4-benzodiazepine-7-carboxamide;

(2R)-N-[(1-methyl-1H-indol-2-yl)methyl]-3-oxo-N,2,4-trimethyl-2,3,4,5-tetrahydro-1H-1,4-benzodiazepine-7-carboxamide;

(2R)-2-benzyl-N,4-dimethyl-N-[(1-methyl-1H-indol-2-yl)methyl]-3-oxo-2,3,4,5-tetrahydro-1H-1,4-benzodiazepine-7-carboxamide;

(2R)-2-[(carbomethoxy)methyl]-N,4-dimethyl-N-[[1-(4-hydroxybenzyl)-1H-indol-2-yl]methyl]-3-oxo-2,3,4,5-tetrahydro-1H-1,4-benzodiazepine-7-carboxamide;

(2R)-N-[[1-(4-hydroxybenzyl)-1H-indol-2-yl]methyl]-3-oxo-N,2,4-trimethyl-2,3,4,5-tetrahydro-1H-1,4-benzodiazepine-7-carboxamide;

(2R)-N,4-dimethyl-2-(hydroxymethyl)-N-[(1-methyl-1H-indol-2-yl)methyl]-3-oxo-2,3,4,5-tetrahydro-1H-1,4-benzodiazepine-7-carboxamide;

N,4-dimethyl-N-[(1-methyl-1H-indol-2-yl)methyl]-3-oxo-2,3,4,5-tetrahydro-1H-1,4-benzodiazepine-7-carboxamide;

(2R)-N,4-dimethyl-N-[[1-(4-hydroxybenzyl)-1H-indol-2-yl]methyl]-2-(hydroxymethyl)-3-oxo-2,3,4,5-tetrahydro-1H-1,4-benzodiazepine-7-carboxamide;

(2R)-N,4-dimethyl-N-[(5-benzyloxy-1-methyl-1H-indol-2-yl)methyl]-2-(hydroxymethyl)-3-oxo-2,3,4,5-tetrahydro-1H-1,4-benzodiazepine-7-carboxamide;

(2R)-N,4-dimethyl-N-2-(hydroxymethyl)-[(5-hydroxy-1-methyl-1H-indol-2-yl)methyl]-3-oxo-2,3,4,5-tetrahydro-1H-1,4-benzodiazepine-7-carboxamide;

(2R)-N,4-dimethyl-N-[(1-methyl-1H-indol-2-yl)methyl]-3-oxo-2-propyl-2,3,4,5-tetrahydro-1H-1,4-benzodiazepine-7-carboxamide;

(2R)-4-benzyl-2-(hydroxymethyl)-N-methyl-N-[(1-methyl-1H-indol-2-yl)methyl]-3-oxo-2,3,4,5-tetrahydro-1H-1,4-benzodiazepine-7-carboxamide; and (2R)-2-(hydroxymethyl)-N-methyl-N-[(1-methyl-1H-indol-2-yl)methyl]-3-oxo-4-phenethyl-2,3,4,5-tetrahydro-1H-1,4-benzodiazepine-7-carboxamide; or pharmaceutically acceptable salts thereof.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

$C_{1-4}$alkyl as applied herein means an optionally substituted alkyl group of 1 to 4 carbon atoms, and includes methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g., that a covalent bond is present).

Any $C_{1-4}$alkyl or $C_{1-6}$ alkyl, $C_{2-6}$ alkenyl, $C_{2-6}$ alkynyl or $C_{1-6}$ oxoalkyl may be optionally substituted with the group $R^x$, which may be on any carbon atom that results in a stable structure and is available by conventional synthetic techniques. Suitable groups for $R^x$ are $C_{1-4}$alkyl, OR', SR', $C_{1-4}$alkylsulfonyl, $C_{1-4}$alkylsulfoxyl, —CN, N(R')$_2$, CH$_2$N(R')$_2$, —NO$_2$, —CF$_3$, —CO$_2$R'—CON(R')$_2$, —COR', —NR'C(O)R', F, Cl, Br, I, or $CF_3S(O)_r$—, wherein r is 0, 1 or 2.

Halogen or halo means F, Cl, Br, and I.

Ar, or aryl, as applied herein, means phenyl or naphthyl, or phenyl or naphthyl substituted by one to three substituents, such as those defined above for alkyl, especially $C_{1-4}$alkyl, $C_{1-4}$alkoxy, $C_{1-4}$alkthio, CF$_3$, NH$_2$, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydro-quinoline and iso-quinoline. Any accessible combination of up to three substituents on the Het ring, such as those defined above for alkyl that are available by chemical synthesis and are stable are within the scope of this invention.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as those defined above for alkyl, on the cycloalkyl ring that is available by conventional chemical synthesis and is stable, is within the scope of this invention.

Certain radical groups are abbreviated herein. t-Bu refers to the tertiary butyl radical, Boc refers to the t-butyloxycarbonyl radical, Fmoc refers to the fluorenyl-methoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of formula (II) with a compound of formula (III):

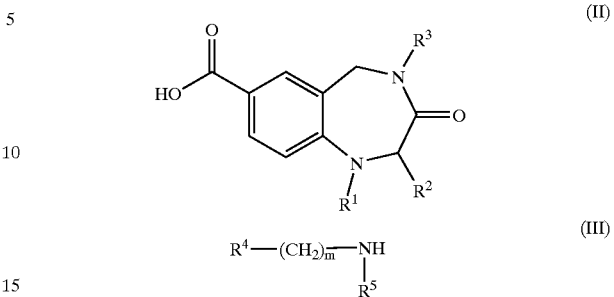

wherein $R^1$, $R^2$, $R^3$, $R^4$, $R^5$ and m are as defined in formula (I), with any reactive functional groups protected, with an amide coupling reagent;

and thereafter removing any protecting groups, and optionally forming a pharmaceutically acceptable salt.

In particular, compounds of the formula (I) are prepared by the general methods described in Scheme I.

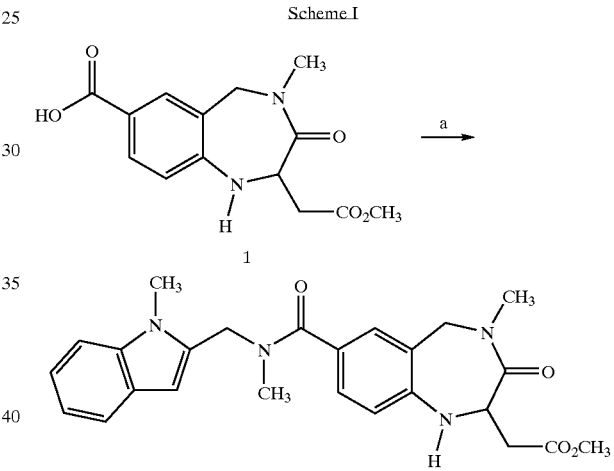

a) 1-methyl-2-(methylaminomethyl)indole, HOBT, I-Pr$_2$NEt, EDC, DMF.

Compound I-1, the preparation of which follows the general procedures outlined in Bondinell, et al. (WO 93/00095) and Bondinell, et al. (WO 94/14776) and the procedures detailed in Miller, et al., *Tetrahedron Lett*. 1995, 36, 9433–9436, is converted to an activated form of the carboxylic acid using, for example, EDC and HOBT, and the activated form is subsequently reacted with 1-methyl-2-(methylaminomethyl)indole to afford the corresponding amide I-2. Many additional methods for converting a carboxylic acid to an amide are known, and can be found in standard reference books, such as "Compendium of Organic Synthetic Methods", Vol. I–VI (published by Wiley-Interscience).

The formula (I) compounds of the present invention may also be prepared by methods analogous to those described in Bondinell, et al., PCT application WO 93/00095, published Jan. 7, 1993 and Bondinell, et al., PCT application WO 94/14776, published Jul. 7, 1994. Reference should be made to said patent applications for their full disclosure, particularly to the methods of preparing the compounds therein, said disclosures being incorporated herein by reference.

Amide coupling reagents as used herein denote reagents which may be used to form peptide bonds. Typical coupling methods employ carbodiimides, activated anhydrides and esters and acyl halides. Reagents such as EDC, DCC, DPPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Typically, the amine or aniline is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran (THF), in the presence of a base, such as N-methyl morpholine, DMAP or a trialkylamine, with isobutyl chloroformate to form the "activated anhydride", which is subsequently reacted with the free amine of a second protected amino acid or aniline.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients, such as cocoa butter, glycerin, gelatin or polyethylene glycols, and molded into a suppository.

For topical administration, the compounds of this invention may be combined with diluents to take the form of ointments, gels, pastes, creams, powders or sprays. The compositions which are ointments, gels, pastes or creams contain diluents, for example, animal and vegetable fats, waxes, paraffins, starch, tragacanth, cellulose derivatives, polyethylene glycols, silicones, bentonites, silicic acid, talc and zinc oxide, or mixtures of these substances. The compositions which are powders or sprays contain diluents, for example, lactose, talc, silicic acid, aluminum hydroxide, calcium silicate and polyamide powder, or mixtures of these substances. Additionally, for topical ophthalmologic administration, the typical carriers are water, mixtures of water and water miscible solvents, such as lower alkanols or vegetable oils, and water-soluble non-toxic polymers, for example cellulose derivatives, such as methyl cellulose.

The compounds described herein are inhibitors of Fab I, and are useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Also, the compounds of this invention may be useful as antifungal agents. Additionally, the compounds may be useful in combination with known antibiotics.

The compounds of this invention are administered to the patient, in a manner such that the concentration of drug is sufficient to treat bacterial infections. The pharmaceutical composition containing the compound is administered at an oral dose of between about 10 mg to about 1000 mg, taken once or several times daily, in a manner consistent with the condition of the patient. Preferably, the oral dose would be about 50 mg to about 500 mg, although the dose may be varied depending upon the age, body weight and symptoms of the patient. For acute therapy, parenteral administration is preferred. An intravenous infusion of the compound of formula (I) in 5% dextrose in water or normal saline, or a similar formulation with suitable excipients, is most effective, although an intramuscular bolus injection is also useful. The precise level and method by which the compounds are administered is readily determined by one skilled in the art.

The compounds may be tested in one of several biological assays to determine the concentration of compound which is required to have a given pharmacological effect.

Cloning of S. aureus FabI:

The fabI gene was cloned from the chromosomal DNA of S. aureus strain WCUH29 using the polymerase chain reaction. Amplification was performed using Taq DNA polymerase (BRL) and the following primers: 5'-CGC CTCGAGATGTTAAATCTTGAAAACAAAACATATGTC-3' and 5'-CGC GGATCCAATCAAGTCAGGTTGAAATATCCA-3' (XhoI and BamHI sites underlined). The resulting fragment was then digested with XhoI and BamHI and ligated into XhoI- and BamHI-digested expression vector pET-16b (Novagen), producing pET-His$_{10}$-fabI. The gene sequence of fabI was confirmed by automated cycle sequencing using an Applied Biosystems model 377 machine. The untagged version of pET-fabI was constructed by digesting pET-His$_{10}$-fabI with NcoI and NdeI to remove a 97 bp fragment encoding the His 10 tag, the factor Xa cleavage site and the first 8 amino acids of FabI, and replacing it with a linker encoding the first 8 amino acids of FabI plus a glycine residue between the initiator methionine and the lysine at position 2. This plasmid was called pET-fabI. The linker was made by annealing the following two oligonucleotides: 5'-CATGGGCTTAAATCTTGAAAACAAAACA-3' and 5'-TATGTTTTGTTTTCAAGATTTAAGCC-3'. The linker sequence in pET-fabI was confirmed by dideoxy sequencing. Only native FabI was used for compound evaluation. For overproduction of native FabI, plasmid pET-fabI was transformed into BL21 (DE3) (Novagen) cells, to form strain BL21(DE3):pET-fabI.

Purification of S. aureus FabI

S. aureus FabI was expressed as soluble protein to 10% of total cell protein, 400 g cells being recovered from 15L fermentation in tryptone phosphate medium. The cells were lysed and the sample centrifuged. The resulting supernatant was filtered and purified using three consecutive chromatography columns: ion-exchange (Sourse 15Q), dye-affinity (Blue sepharose), and size exclusion chromatography columns (Superose 12). After each column the FabI containing fractions were pooled, concentrated, and checked for purity and biological activity.

Cloning of E. coli FabI:

A PCR fragment of correct size for E. coli FabI was PCR amplified from E. coli chromosomal DNA, subcloned into the TOPO TA cloning vector, and verified by colony PCR+ restriction endonuclease analysis. The presumptive E. coli FabI PCR fragment was subcloned into the expression vector pBluePet. The FabI clone was transformed into E. coli strain BL21 (DE3). Small Scale expression studies show an over-expressed protein band of correct molecular weight (~28 Kda) for E. coli FabI clearly visible following Coomassie staining of SDS PAGE gels. DNA sequencing of the E. coli FabI expression constructs illustrated that no errors were apparent. N' terminal amino acid sequencing has confirmed the over-expressed protein band to be E. coli FabI.

Purification of E. coli FabI

E. coli FabI was expressed as soluble protein to 15% of total cell protein, 120 g cells being recovered from 3L fermentation in shake flasks in modified terrific broth. The cells were lysed and the sample centrifuged. The resulting supernatant was filtered and purified using three consecutive chromatography columns: ion-exchange (Sourse 15Q), dye-affinity (blue sepharose), and size exclusion (superose 12). After each column the FabI containing fractions were pooled, concentrated and checked for purity and biological activity.

S aureus FabI Enzyme Inhibition Assay:

Assays were carried out in half-area, 96-well microtitre plates. Compounds were evaluated in 50-uL assay mixtures containing 100 mM NaADA, pH 6.5 (ADA =N-[2-acetamido]-2-iminodiacetic acid), 4% glycerol, 0.25 mM crotonoyl CoA, 1 mM NADH, and an appropriate dilution of S. aureus FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. IC$_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have IC$_{50}$'s from about 15.0 micromolar to about 0.15 micromolar.

E. coli FabI Enzyme Inhibition Assay:

Assays were carried out in half-area, 96-well microtitre plates. Compounds were evaluated in 150-uL assay mixtures containing 100 mM NaADA, pH 6.5 (ADA=N-[2-acetamido]-2-iminodiacetic acid), 4% glycerol, 0.25 mM crotonoyl CoA, 50 uM NADH, and an appropriate dilution of E. coli FabI. Inhibitors were typically varied over the range of 0.01–10 uM. The consumption of NADH was monitored for 20 minutes at 30° C. by following the change in absorbance at 340 nm. Initial velocities were estimated from an exponential fit of the non-linear progress curves represented by the slope of the tangent at t=0 min. IC$_{50}$'s were estimated from a fit of the initial velocities to a standard, 4-parameter model and are typically reported as the mean±S.D. of duplicate determinations. Triclosan, a commercial antibacterial agent and inhibitor of FabI, is currently included in all assays as a positive control. Compounds of this invention have IC$_{50}$'s from about 5.0 micromolar to about 0.10 micromolar.

Antimicrobial Activity Assay:

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compound was tested in serial two-fold dilutions ranging from 0.06 to 64 mcg/mL. A panel of 12 strains were evaluated in the assay. This panel consisted of the following laboratory strains: Staphylococcus aureus Oxford, Streptococcus pneumoniae R6, Streptococcus pyogenes CN10, Enterococcus faecalis I, Haemophilus influenzae Q1, Escherichia coli DC0, E. coli ESS, E. coli 7623 (AcrAB$^+$), E. coli 120 (AcrAB$^-$) Klebsiella pneumoniae E70, Pseudomonas aeruginosa K799 wt and Candida albicans GRI 681. The minimum inhibitory concentration (MIC) was determined as the lowest concentration of compound that inhibited visible growth. A mirror reader was used to assist in determining the MIC endpoint.

One skilled in the art would consider any compound with a MIC of less than 256 µg/mL to be a potential lead compound. Preferably, the compounds used in the antimicrobial assays of the present invention have a MIC value of less than 128 µg/mL. Most preferably, said compounds have a MIC value of less than 64 µg/mL.

The examples which follow are intended in no way to limit the scope of this invention, but are provided to illustrate how to make and use the compounds of this invention. Many other embodiments will be readily apparent to those skilled in the art.

EXAMPLES

General

Proton nuclear magnetic resonance ($^1$H NMR) spectra were recorded at 300 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. $CDCl_3$ is deuteriochloroform, $DMSO\text{-}d_6$ is hexadeuteriodimethylsulfoxide, and $CD_3OD$ is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230–400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

(2R)-2-[(Carbomethoxy)methyl]-4-methyl-3-oxo-2,3,4,5-tetrahydro-1H-1,4-benzodiazepine-7-carboxylic acid and (2S)-2-(carbomethoxymethyl)-4-methyl-3-oxo-2,3,4,5-tetrahydro-1H-1,4-benzodiazepine-7-carboxylic acid were prepared as described by the procedures outlined in Bondinell, et al. (WO 93/00095) and Bondinell, et al. (WO 94/14776). Also see the procedures detailed in Miller, et al., *Tetrahedron Lett.* 1995, 36, 9433–9436.

Preparation 1

Preparation of 1-methyl-2-(methylaminomethyl) indole a) N,1-Dimethylindole-2-carboxamide To a stirred solution of ethyl indole-2-carboxylate (25.0 g, 132.1 mmole) in dry DMF (100 mL) at 5° C. was added 60% NaH (6.9 g, 171.7 mmole). After 10 min, methyl iodide (56.2 g, 396.3 mmole) was added and the reaction slurry was allowed to warm RT and stirred for 12 hr. The reaction contents were poured into $H_2O$ (200 mL) and extracted with EtOAc (2×150 mL). The combined organic phases were washed sequentially with $H_2O$ and brine, then were dried over $Na_2SO_4$. Concentration under reduced pressure gave a yellow oil. This oil was suspended in a 40% methylamine/$H_2O$ solution (100 mL) containing THF (50 mL) and stirred vigorously at RT for 24 hr. The reaction solution was concentrated under vacuum to remove the THF and then poured into $H_2O$ (400 mL). The precipitate was filtered, washed with $H_2O$ and dried under vacuum at RT to afford the title compound (23.3 g, 94%) as a white solid: MS (ES) m/e 189 $(M+H)^+$.

b) 1-Methyl-2-(methylaminomethyl)indole

To a solution of N,1-dimethylindole-2-carboxamide (23.3 g, 124.2 mmole) in dry THF (400 mL) was added $LiAlH_4$ (1.0 M in THF, 250 mL, 250 mmole). The reaction solution was heated to 70° C. under argon for 36 hr with stirring. The resulting white cloudy solution was allowed to cool to RT and then was submitted to a basic work-up according to the procedure of Micovic and Mihailovic (Micovic, V. M.; M. L. J. *J. Org. Chem.* 1956, 18, 1190). Purification by chromatography on silica gel (5% $NH_4OH$ in 9:1 $CHCl_3$/MeOH) afforded the titled compound (15.8 g, 73%) as a colorless oil: MS (ES) m/e 175 $(M+H)^+$.

Preparation 2

Preparation of 5-benzyloxy-1-methyl-2-(methylaminomethyl)indole a) 5-Benzyloxy-N,1-dimethylindole-2-carboxamide According to the procedure of Preparation 1 (a), except substituting ethyl 5-(benzyloxy)indole carboxylate (40.8 g, 132.0 mmole) for the ethyl indole-2-carboxylate, the title compound (37.4 g, 96%) was prepared as a white solid: MS (ES) m/e 295 $(M+H)^+$.

b) 5-Benzyloxy-1-methyl-2-(methylaminomethyl)indole

According to the procedure of Preparation 1 (b), except substituting 5-benzyloxy-N,1-dimethylindole-2-carboxamide (37.4 g, 126.7 mmole) for the N,1-dimethylindole-2-carboxamide, the title compound (24.5 g, 69%) was prepared as a white solid: MS (ES) m/e 281 $(M+H)^+$.

Preparation 3

Preparation of 1-(4-hydroxybenzyl)-2-(methylaminomethyl)indole a) 1-(4-Benzyloxybenzyl)-N-methylindole-2-carboxamide According to the procedure of Preparation 1 (a), except substituting 4-benzyloxybenzyl chloride (33.8 g, 145.2 mmole) for methyl iodide, the title compound (44.4 g, 91%) was prepared as a white solid: MS (ES) m/e 371 $(M+H)^+$.

b) 1-(4-Benzyloxybenzyl)-2-(methylaminomethyl)indole

According to the procedure of Preparation 1 (b), except substituting 1-(4-benzyloxybenzyl)-N-methylindole-2-carboxamide (44.4 g, 120.1 mmole) for the N,1-dimethylindole-2-carboxamide, the title compound (27.0 g, 63%) was prepared as a white solid: MS (ES) m/e 358 $(M+H)^+$.

c) 1-(4-Hydroxybenzyl)-2-(methylaminomethyl)indole

To a solution of 1-(4-benzyloxybenzyl)-2-(methylaminomethyl)indole (27.1 g, 75.9 mmole) in methanol (75 mL) at RT in a Parr hydrogenation flask was added 10% Pd/C (0.5 g). The reaction mixture was shaken under 45 psi of $H_2$ for 4 hr. The suspension was filtered through celite®, and the filter pad was washed with methanol. The filtrate was concentrated on the rotavap, and the residue was dried under high vacuum to afford the titled compound (18.0 g, 89%) as an off-white solid: MS (ES) m/e 268 $(M+H)^+$.

Preparation 4

Preparation of tert-butyl (2R)-2,4-dimethyl-3-oxo-2,3,4,5-tetrahydro-1H-1,4-benzodiazepine-7-carboxylate a) tert-Butyl 4-fluoro-3-methylbenzoate To a stirred solution of di-tert-butyl dicarbonate (11 g, 50.4 mmole) in dry THF (50 mL) with stirring under argon at −78° C. was added over 5 min a 1.0 M solution of 4-fluoro-3-methylphenylmagnesium bromide in THF (50 mL, 50 mmole). After 15 min the cooling bath was removed and the reaction was allowed to warm to RT. After 4 h at RT the reaction was concentrated to dryness on the rotavap. The residue was taken up in $Et_2O$ (250 mL) and washed sequentially with 1.0 N NaOH (250 mL) and brine (250 mL). Drying ($MgSO_4$) and concentration left an oil that was distilled through a short path distillation apparatus under high vacuum. The fraction boiling at 92–95° C./1 mm Hg was collected to give the title compound (9.85 g, 94%) as a clear oil: $^1H$ NMR (300 MHz, $CDCl_3$) δ 7.78–7.85 (m, 2H), 7.02 (t, J=1.8 Hz, 1H), 2.30 (d, J=1.8 Hz, 3H), 1.59 (s, 9H).

b) tert-Butyl 4-fluoro-3-(methylaminomethyl)benzoate

A mixture of tert-butyl 4-fluoro-3-methylbenzoate (9.85 g, 46.9 mmole), N-bromosuccinimide (10 g, 56 mmole), benzoyl peroxide (0.6 g, 2.5 mmole), and $CCl_4$ (100 mL)

was heated to reflux with the aid of a 150 W tungsten flood lamp. After refluxing for 24 h, the reaction was cooled to RT and filtered, and the filter pad was washed with $CCl_4$ (25 mL). The filtrate was concentrated to give the crude benzylic bromide (15.11 g, 59% pure by GC, containing 32% dibromide) as a yellow oil. To a solution of this crude bromide in THF (150 mL) was added with stirring at 0° C. a solution of methylamine (40 wt % in $H_2O$, 20 mL, 232 mmole) in one portion. The reaction was allowed to warm to RT and stirred for 18 h, then was concentrated to half its volume. The residue was diluted with $H_2O$ (250 mL) and extracted with $Et_2O$ (2×150 mL). The combined organic layers were washed sequentially with 1.0 N NaOH (150 mL) and brine (150 mL), dried ($Na_2SO_4$), and concentrated. The remaining residue was purified by flash chromatography on silica gel (10% MeOH in 1:1 EtOAc/$CHCl_3$) to give the title compound (4.85 g, 43%) as a yellow oil: MS (ES) m/e 240.0 $(M+H)^+$.

c) tert-Butyl (R)-4-fluoro-3-[[[N-(benzyloxycarbonyl)-alaninyl]methylamino]methyl]benzoate To a stirred solution of tert-butyl 4-fluoro-3-(methylaminomethyl)benzoate (2.42 g, 10.1 mmole) in DMF (75 mL) was added N-(benzyloxycarbonyl)-D-alanine (2.45 g, 11 mmole) and $HOBt.H_2O$ (1.5 g, 11 mmole), followed by DCC (2.4 g, 11.6 mmole). The reaction was stirred for 16 h then was concentrated to dryness. Purification by flash chromatography on silica gel (30% EtOAc/hexanes) gave the title compound (3.29 g, 73%) as a clear oil: $^1$H NMR (300 MHz, $CDCl_3$) mixture of amide rotamers δ 7.90–7.95 (m, 1H), 7.81 (dd, 1H), 7.31–7.32 (m, 5H), 7.08 (t, 1H), 5.72 & 5.83 (2 d, J=7.8 Hz, 1H), 5.11 (s, 2H), 4.89 (d, J=15.3 Hz, 1H), 4.72–4.77 (m, 1H), 4.47 (d, J=15.3 Hz, 1H), 2.92 & 3.05 (2s, 3H), 1.56 (s, 9H), 1.37 & 1.40(2 d, J=6.8 Hz, 3H).

d) tert-Butyl (2R)-2,4-dimethyl-3-oxo-2,3,4,5-tetrahydro-1H-1,4-benzodiazepine-7-carboxylate A mixture of tert-butyl (R)-4-fluoro-3-[[[N-(benzyloxycarbonyl)-alaninyl]methylamino]methyl] benzoate (3.29 g, 7.4 mmole), 10% Pd/C (1.0 g, 0.9 mmole), and MeOH (75 mL) was shaken at RT under $H_2$ (50 psi) on a Parr apparatus. After 4 h, the reaction was filtered through celite®, and the filter pad was washed with MeOH. The filtrate was concentrated, and the remaining residue was taken up in dry DMSO (75 mL). The solution was evacuated and purged with argon (3×), then was heated with stirring at 125° C. for 24 h. Most of the DMSO was removed by distillation under vacuum, and the remaining solution was diluted with EtOAc (100 mL). The solution was washed sequentially with saturated $NaHCO_3$ (100 mL) and brine (100 mL), dried ($Na_2SO_4$), and concentrated. The remaining residue was purified by flash chromatography on silica gel (50% EtOAc/hexanes) to give the title compound (1.41 g, 66%) as a white solid: MS (ES) m/e 291.1 $(M+H)^+$, 581.2 $(2M+H)^+$.

Preparation 5

Preparation of Tert-butyl (2R)-2-benzyl-4-methyl-3-oxo-2,3,4,5-tetrahydro-1H-1,4-benzodiazepine-7-carboxylate a) tert-Butyl (R)-4-fluoro-3-[[[N-(benzyloxycarbonyl) phenylalaninyl]-methylamino]methyl]benzoate According to the procedure of Preparation 4 (c), except substituting N-(benzyloxycarbonyl)-D-phenylalanine (3.30 g, 11 mmole) for the N-(benzyloxycarbonyl)-D-alanine, the title compound (4.35 g, 81%) was prepared as a colorless oil following flash chromatography on silica gel (30% EtOAc/hexanes): $^1$H NMR (300 MHz, $CDCl_3$) mixture of amide rotamers δ 7.91–7.95 (m, 2H), 7.25–7.34 (m, 5H), 7.04–7.19 (m, 6H), 5.70 & 5.65 (2 d, 1H), 4.92–5.10 (m, 2H), 4.58 (dd, 1H), 3.01 (d, J=7.0 Hz, 2H), 2.65 & 2.84 (2 s, 3H), 1.56 & 1.58 (2 s, 9H).

b) tert-Butyl (2R)-2-benzyl-4-methyl-3-oxo-2,3,4,5-tetrahydro-1H-1,4-benzodiazepine-7-carboxylate According to the procedure of Preparation 4 (d), except substituting tert-butyl (R)-4-fluoro-3-[[[N-(benzyloxycarbonyl)phenylalaninyl]methylamino]methyl] benzoate (4.35 g, 8.2 mmole) for the tert-butyl (R)-4-fluoro-3-[[[N-(benzyloxycarbonyl)alaninyl]methylamino]methyl] benzoate, the title compound (1.91 g, 64%) was prepared as a white solid following flash chromatography on silica gel (35% EtOAc/hexanes): MS (ES) m/e 367.2 $(M+H)^+$.

Preparation 6

Preparation of Tert-butyl(2R)-2-hydroxymethyl-4-methyl-3-oxo-2,3,4,5-tetrahydro-1H-1,4-benzodiazepine-7-carboxylate a) tert-Butyl (R)-4-fluoro-3-[[[N-(benzyloxycarbonyl) serinyl]methylamino]methyl]benzoate According to the procedure of Preparation 4 (c), except using tert-butyl 4-fluoro-3-(methylaminomethyl)benzoate (4.00 g, 16.7 mmole), N-(benzyloxycarbonyl)-D-serine (4.00 g, 16.7 mmole), $HOBt.H_2O$ (2.3 g, 17 mmole), DCC (2.4 g, 11.6 mmole), and 1:1 DMF/$CH_2Cl_2$ (100 mL), the title compound (6.60 g, 79%) was prepared as a sticky foam following flash chromatography on silica gel (50% EtOAc/hexanes): MS (ES) m/e 461.1 $(M+H)^+$.

b) Tert-Butyl (2R)-2-benzyl-4-methyl-3-oxo-2,3,4,5-tetrahydro-1H-1,4-benzodiazepine-7-carboxylate According to the procedure of Preparation 4 (d), except substituting tert-butyl (R)-4-fluoro-3-[[[N-(benzyloxycarbonyl)serinyl]methylamino]methyl]benzoate (6.06 g, 13.2 mmole) for tert-butyl (R)-4-fluoro-3-[[[N-(benzyloxycarbonyl)alaninyl]methylamino]methyl] benzoate, the title compound (2.24 g, 53%) was prepared as a white solid following flash chromatography on silica gel (70% EtOAc/hexanes): MS (ES) m/e 307.0 $(M+H)^+$.

Preparation 7

Preparation of Tert-butyl 4-methyl-3-oxo-2,3,4,5-tetrahydro-1H-1,4-benzodiazepine-7-carboxylate a) Tert-Butyl 4-fluoro-3-[[[N-(benzyloxycarbonyl)glycinyl] methylamino]methyl]benzoate According to the procedure of Preparation 4 (c), except using tert-butyl 4-fluoro-3-(methylaminomethyl)benzoate (4.00 g, 16.7 mmole), N-(benzyloxycarbonyl)glycine (3.50 g, 16.7 mmole), $HOBt.H_2O$ (2.3 g, 17 mmole), DCC (2.4 g, 11.6 mmole), and 1:1 DMF/$CH_2Cl_2$ (100 mL), the title compound (7.26 g, 100%) was prepared as a thick yellow oil following flash chromatography on silica gel (30% EtOAc/hexanes): MS (ES) m/e 431.02 $(M+H)^+$.

b) Tert-Butyl 4-methyl-3-oxo-2,3,4,5-tetrahydro-1H-1,4-benzodiazepine-7-carboxylate According to the procedure of Preparation 4 (d), except substituting tert-butyl 4-fluoro-3-[[[N-(benzyloxycarbonyl) glycinyl]methylamino]methyl]benzoate for the tert-butyl (R)-4-fluoro-3-[[[N-(benzyloxycarbonyl)alaninyl] methylamino]methyl]benzoate, the title compound (2.26 g, 48%) was prepared as a white solid following flash chromatography on silica gel (80% EtOAc/hexanes): $^1$H NMR (300 MHz, DMSO-$d_6$) δ7.52 (s, 1H), 7.50 (dd, 1H), 6.95 (br s, 1H), 6.50 (d, J=8.1 Hz, 1H), 4.61 (s, 2H), 4.08 (s, 2H), 2.92 (s, 3H), 1.51 (s, 9H).

Preparation 8

Preparation of Tert-butyl (2R)-4-methyl-3-oxo-2-propyl-2,3,4,5-tetrahydro-1H-1,4-benzodiazepine-7-carboxylate a) Tert-Butyl (R)-4-fluoro-3-[[[N-(benzyloxycarbonyl)-norvalinyl]methylamino]methyl]benzoate According to the procedure of Preparation 4 (c), except using tert-butyl 4-fluoro-3-(methylaminomethyl)benzoate (4.00 g, 16.7 mmole), N-(benzyloxycarbonyl)-D-norvaline (4.20 g, 16.7 mmole), HOBt.H$_2$O (2.3 g, 17 mmole), Et$_3$N (2.4 mL, 17.1 mmole), EDC.HCl (3.3 g, 17.2 mmole), and 1:1 DMF/CH$_2$Cl$_2$ (100 mL), the title compound (7.68 g, 97%) was prepared as a thick yellow oil following flash chromatography on silica gel (30% EtOAc/hexanes): $^1$H NMR (300 MHz, DMSO-d$_6$) mixture of amide rotamers δ 7.81–7.92 (m, 1H), 7.70–7.80 (m, 1H), 7.52–7.65 (m, 1H), 7.25–7.38 (m, 5H), 4.62–5.08 (m, 3 H), 4.38–4.53 (m, 2H), 2.83 & 3.07(2s, 3H), 1.52–1.58 (m, 2H), 1.52 (s, 9H), 1.15–1.37 (m, 2H), 0.74 & 0.87 (2 t, 3H).

b) Tert-Butyl (2R)-4-methyl-3-oxo-2-propyl-2,3,4,5-tetrahydro-1H-1,4-benzodiazepine-7-carboxylate According to the procedure of Preparation 4 (d), except substituting tert-butyl (R)-4-fluoro-3-[[[N-(benzyloxycarbonyl)norvalinyl]methylamino]methyl] benzoate (7.68 g, 16.3 mmole) for the tert-butyl (R)-4-fluoro-3-[[[N-(benzyloxycarbonyl)alaninyl]methylamino]methyl]benzoate, the title compound (1.86 g, 48%) was prepared as a white solid following recrystallization from EtOAc/hexanes: MS (ES) m/e 319.3 (M+H)$^+$.

Preparation 9

Preparation of Tert-butyl (2R)-4-benzyl-2-hydroxymethyl-3-oxo-2,3,4,5-tetrahydro-1H-1,4-benzodiazepine-7-carboxylate a) Tert-Butyl 4-fluoro-3-(benzylaminomethyl)benzoate According to the procedure of Preparation 4 (b), except using tert-butyl 4-fluoro-3-methylbenzoate (6.25 g, 29.7 mmole), N-bromosuccinimide (5.75 g, 32.3 mmole), benzoyl peroxide (375 mg, 1.6 mmole), CCl$_4$ (50 mL), and benzylamine (17 mL, 156 mmole), the title compound (5.70 g, 60%) was prepared as a yellow oil following flash chromatography on silica gel (20% EtOAc/hexanes): MS (ES) m/e 316.1 (M+H)$^+$.

b) Tert-Butyl (R)-4-fluoro-3-[[[N-(benzyloxycarbonyl) serinyl]-benzylamino]methyl]benzoate According to the procedure of Preparation 4 (c), except using tert-butyl 4-fluoro-3-(benzylaminomethyl)benzoate (4.80 g, 15.2 mmole), N-(benzyloxycarbonyl)-D-serine (3.83 g, 16 mmole), HOBt.H$_2$O (2.16 g, 16 mmole), Et$_3$N (2.24 mL, 16 mmole), EDC.HCl (3.07 g, 16 mmole), and 1:1 DMF/CH$_2$Cl$_2$ (75 mL), the title compound (1.58 g, 19%) was prepared as a thick oil following flash chromatography on silica gel (40% EtOAc/hexanes): $^1$H NMR (300 MHz, DMSO-d$_6$) mixture of amide rotamers δ 7.39–8.18 (m, 2H), 7.18–7.37 (m, 11H), 4.25–5.11 (m, 7H), 3.33–4.04 (m, 2H), 1.53 (s, 9H).

c) Tert-Butyl (2R)-4-benzyl-2-hydroxymethyl-3-oxo-2,3,4,5-tetrahydro-1H-1,4-benzodiazepine-7-carboxylate According to the procedure of Preparation 4 (d), except substituting tert-butyl (R)-4-fluoro-3-[[[N-(benzyloxycarbonyl)serinyl]benzylamino]methyl]benzoate (1.58 g, 3 mmole) for the tert-butyl (R)-4-fluoro-3-[[[N-(benzyloxycarbonyl)alaninyl]-methylamino]methyl] benzoate, the title compound (0.39 g, 34%) was prepared as an off-white solid following recrystallization from EtOAc/hexanes: MS (ES) m/e 383.0 (M+H)$^+$.

Preparation 10

Preparation of tert-butyl (2R)-2-hydroxymethyl-3-oxo-4-phenethyl-2,3,4,5-tetrahydro-1H-1,4-benzodiazepine-7-carboxylic Acid a) Tert-Butyl 4-fluoro-3-[(phenethylamino)methyl]benzoate According to the procedure of Preparation 4 (b), except using tert-butyl 4-fluoro-3-methylbenzoate (6.25 g, 29.7 mmole), N-bromosuccinimide (5.75 g, 32.3 mmole), benzoyl peroxide (375 mg, 1.6 mmole), CCl$_4$ (50 mL), and 2-phenethylamine (19 mL, 151 mmole), the title compound (6.32 g, 64%) was prepared as a yellow oil following flash chromatography on silica gel (gradient: 20–40% EtOAc/hexanes): MS (ES) m/e 330.1 (M+H)$^+$.

b) Tert-Butyl (R)-4-fluoro-3-[[[N-(benzyloxycarbonyl) serinyl]-phenethylamino]methyl]benzoate According to the procedure of Preparation 4 (c), except using tert-butyl 4-fluoro-3-[(phenethylamino)methyl] benzoate (5.00 g, 15.2 mmole), N-(benzyloxycarbonyl)-D-serine (3.83 g, 16 mmole), HOBt.H$_2$O (2.16 g, 16 mmole), Et$_3$N (2.24 mL, 16 mmole), EDC.HCl (3.07 g, 16 mmole), and 1:1 DMF/CH$_2$Cl$_2$ (75 mL), the title compound (3.44 g, 41%) was prepared as a thick oil following flash chromatography on silica gel (40% EtOAc/hexanes): $^1$H NMR (300 MHz, DMSO-d$_6$) mixture of amide rotamers δ 7.31–8.18 (m, 2H), 7.19–7.29 (m, 11H), 4.86–5.11 (m, 4H), 4.33–4.79 (m, 3H), 3.49–3.80 (m, 4 H), 1.51 (s, 9H).

c) Tert-Butyl (2R)-2-hydroxymethyl-3-oxo-4-phenethyl-2,3,4,5-tetrahydro-1H-1,4-benzodiazepine-7-carboxylic Acid According to the procedure of Preparation 4 (d), except substituting tert-butyl (R)-4-fluoro-3-[[[N-(benzyloxycarbonyl)serinyl]phenethylamino]methyl] benzoate (3.44 g, 6.3 mmole) for the tert-Butyl (R)-4-fluoro-3-[[[N-(benzyloxycarbonyl)alaninyl]-methylamino]methyl] benzoate, the title compound (1.18 g, 47%) was prepared as an off-white solid following recrystallization from EtOAc/hexanes: MS (ES) m/e 397.0 (M+H)$^+$.

Example 1

Preparation of (2R)-2-[(carbomethoxy)methyl]-N,4-dimethyl-N-[(1-methyl-1H-indol-2-yl)methyl]-3-oxo-2,3,4,5-tetrahydro-1H-1,4-benzodiazepine-7-carboxamide a) (2R)-2-[(Carbomethoxy)methyl]-N,4-dimethyl-N-[(1-methyl-1H-indol-2-yl)methyl]-3-oxo-2,3,4,5-tetrahydro-1H-1,4-benzodiazepine-7-carboxamide To a solution of (2R)-2-[(carbomethoxy)methyl]-4-methyl-3-oxo-2,3,4,5-tetrahydro-1H-1,4-benzodiazepine-7-carboxylic acid (0.4 g, 1.37 mmole) in dry DMF (10 mL) at RT was added 1-methyl-2-(methylaminomethyl)indole (0.26 g, 1.50 mmole), HOBt (0.20 g, 1.50 mmole), i-Pr$_2$NEt (0.19 g, 1.50 mmole) and EDC (0.29 g, 1.50 mmole). After 18 hr the reaction solution was diluted with H$_2$O (25 mL) and extracted with EtOAc (2×50 mL). The organic fractions were combined, washed sequentially with H$_2$O and brine, then were dried (Na$_2$SO$_4$). Concentration under vacuum followed by chromatography on silica gel (95:5 CHCl$_3$/MeOH) provided the title compound (0.56 g, 92%) as an off-white solid: MS (ES) m/e 449 (M+H)$^+$.

Example 2

Preparation of (2S)-2-[(carbomethoxy)methyl]-N,4-dimethyl-N-[(1-methyl-1H-indol-2-yl)methyl]-3-oxo-2,3,4,5-tetrahydro-1H-1,4-benzodiazepine-7-carboxamide a) (2S)-2-[(Carbomethoxy)methyl]-N,4-dimethyl-N-[(1-methyl-1H-indol-2-yl)methyl]-3-oxo-2,3,4,5-tetrahydro-1H-1,4-benzodiazepine-7-carboxamide According to the procedure of Example 1 (a), except substituting (2S)-2-[(carbomethoxy)methyl]-4-methyl-3-oxo-2,3,4,5-tetrahydro-1H-1,4-benzodiazepine-7-carboxylic acid (0.4 g, 1.37 mmole) for the (2R)-2-[(carbomethoxy)methyl]-4-methyl-3-oxo-2,3,4,5-tetrahydro-1H-1,4-benzodiazepine-7-carboxylic acid the title compound (0.56 g, 92%) was prepared as an off-white solid: MS (ES) m/e 449 (M+H)$^+$.

Example 3

Preparation of (2R)-2-[(carbomethoxy)methyl-N,4-dimethyl-N-[[1-(4-hydroxybenzyl)-1H-indol-2-yl]methyl]-3-oxo-2,3,4,5-tetrahydro-1H-1,4-benzodiazepine-7-carboxamide a) (2R)-2-[(Carbomethoxy)methyl]-N,4-dimethyl-N-[[1-(4-hydroxybenzyl)-1H-indol-2-yl]methyl]-3-oxo-2,3,4,5-tetrahydro-1H-1,4-benzodiazepine-7-carboxamide According to the procedure of Example 1 (a), except substituting 1-(4-hydroxybenzyl)-2-(methylaminomethyl)indole (0.40 g, 1.50 mmole) for the 1-methyl-2-(methylaminomethyl)indole, the title compound (0.74 g, 91%) was prepared as an off-white solid: MS (ES) m/e 541 (M+H)$^+$.

Example 4

Preparation of (2R)-N-[[1-(4-hydroxybenzyl)-1H-indol-2-yl]methyl]-3-oxo-N,2,4-trimethyl-2,3,4,5-tetrahydro-1H-1,4-benzodiazepine-7-carboxamide a) (2R)-N-[[1-(4-Hydroxybenzyl)-1H-indol-2-yl]methyl]-3-oxo-N,2,4-trimethyl-2,3,4,5-tetrahydro-1H-1,4-benzodiazepine-7-carboxamide According to the procedure of Example 1 (a), except substituting 1-(4-hydroxybenzyl)-2-(methylaminomethyl)indole (0.40 g, 1.50 mmole) for the 1-methyl-2-(methylaminomethyl)indole, and substituting (2R)-2,4-dimethyl-3-oxo-2,3,4,5-tetrahydro-1H-1,4-benzodiazepine-7-carboxylic acid (0.32 g, 1.37 mmole) for the (2R)-2-[(carbomethoxy)methyl]-4-methyl-3-oxo-2,3,4,5-tetrahydro-1H-1,4-benzodiazepine-7-carboxylic acid, the title compound (0.59 g, 90%) was prepared as an off-white solid: MS (ES) m/e 483 (M+H)$^+$.

Example 5

Preparation of (2R)-N,4-dimethyl-N-[[1-(4-hydroxybenzyl)-1H-indol-2-yl]methyl]-2-(hydroxymethyl)-3-oxo-2,3,4,5-tetrahydro-1H-1,4-benzodiazepine-7-carboxamide a) (2R)-N,4-Dimethyl-N-[[1-(4-hydroxybenzyl)-1H-indol-2-yl]methyl]-2-(hydroxymethyl)-3-oxo-2,3,4,5-tetrahydro-1H-1,4-benzodiazepine-7-carboxamide According to the procedure of Example 1 (a), except substituting 1-(4-hydroxybenzyl)-2-(methylaminomethyl)indole (0.40 g, 1.50 mmole) for the 1-methyl-2-(methylaminomethyl)indole, and substituting (2R)-2-(hydroxymethyl)-4-methyl-3-oxo-2,3,4,5-tetrahydro-1H-1,4-benzodiazepine-7-carboxylic acid (0.34 g, 1.37 mmole) for the (2R)-2-[(carbomethoxy)methyl]-4-methyl-3-oxo-2,3,4,5-tetrahydro-1H-1,4-benzodiazepine-7-carboxylic acid, the title compound (0.63 g, 92%) was prepared as an off-white solid: MS (ES) m/e 499 (M+H)$^+$.

Example 6

Preparation of (2R)-N,4-dimethyl-N-[(5-benzyloxy-1-methyl-1H-indol-2-yl)methyl]-2-(hydroxymethyl)-3-oxo-2,3,4,5-tetrahydro-1H-1,4-benzodiazepine-7-carboxamide a) (2R)-N,4-Dimethyl-N-[(5-benzyloxy-1-methyl-1H-indol-2-yl)methyl]-2-(hydroxymethyl)-3-oxo-2,3,4,5-tetrahydro-1H-1,4-benzodiazepine-7-carboxamide According to the procedure of Example 1 (a), except substituting 5-benzyloxy-1-methyl-2-(methylaminomethyl)indole (0.42 g, 1.50 mmole) for the 1-methyl-2-(methylaminomethyl)indole, and substituting (2R)-2-(hydroxymethyl)-4-methyl-3-oxo-2,3,4,5-tetrahydro-1H-1,4-benzodiazepine-7-carboxylic acid (0.34 g, 1.37 mmole) for the (2R)-2-[(carbomethoxy)methyl]-4-methyl-3-oxo-2,3,4,5-tetrahydro-1H-1,4-benzodiazepine-7-carboxylic acid, the title compound (0.66 g, 94%) was prepared as an off-white solid: MS (ES) m/e 513 (M+H)$^+$.

Example 7

Preparation of (2R)-N,4-dimethyl-N-2-(hydroxymethyl)-[(5-hydroxy-1-methyl-1H-indol-2-yl)methyl]-3-oxo-2,3,4,5-tetrahydro-1H-1,4-benzodiazepine-7-carboxamide a) (2R)-N,4-Dimethyl-N-2-(hydroxymethyl)-[(5-hydroxy-1-methyl-1H-indol-2-yl)methyl]-3-oxo-2,3,4,5-tetrahydro-1H-1,4-benzodiazepine-7-carboxamide To a solution of (2R)-N,4-dimethyl-N-[(5-benzyloxy-1-methyl-1H-indol-2-yl)methyl]-2-(hydroxymethyl)-3-oxo-2,3,4,5-tetrahydro-1H-1,4-benzodiazepine-7-carboxamide (0.40 g, 0.78 mmole) in methanol (40 mL) at RT in a Parr hydrogenation flask was added 10% Pd/C (0.2 g). The reaction mixture was shaken under 45 psi of H$_2$ for 4 hr. The suspension was filtered through celite®, and the filter pad was washed with methanol. The filtrate was concentrated on the rotavap, and the residue was dried under high vacuum to provide the title compound (0.31 g, 95%) as an off-white solid: MS (ES) m/e 423 (M+H)$^+$.

Example 8

Preparation of (2R)-N-[(]-methyl-1H-indol-2-yl)methyl]-3-oxo-N,2,4-trimethyl-2,3,4,5-tetrahydro-1H-1,4-benzodiazepine-7-carboxamide a) (2R)-N-[(1-Methyl-1H-indol-2-yl)methyl]-3-oxo-N,2,4-trimethyl-2,3,4,5-tetrahydro-1H-1,4-benzodiazepine-7-carboxamide To a stirred solution of tert-butyl (2R)-2,4-dimethyl-3-oxo-2,3,4,5-tetrahydro-1H-1,4-benzodiazepine-7-carboxylate (0.75 g, 2.6 mmole) in CH$_2$Cl$_2$ (20 mL) was added trifluoroacetic acid (20 mL). After stirring at RT for 45 min the reaction was concentrated on the rotavap. The residue was redissolved in 4 N HCl in dioxane (50 mL), and the solution was concentrated to dryness. Trituration with Et$_2$O, filtration, and drying under vacuo gave the crude carboxylic acid-hydrochloride salt as a white solid. To a stirred solution of this material in 1:1 DMF/CH$_2$Cl$_2$ (50 mL) was added 1-methyl-2-(methylaminomethyl)indole (0.42 g, 2.6 mmole), Et$_3$N (0.73 mL, 5.2 mmole), HOBt.H$_2$O (0.35 g, 2.6 mmole), and EDC.HCl (0.5 g, 2.6 mmole). After stirring for 18 h the reaction was concentrated on the rotavap, and the residue was taken up in EtOAc (50 mL). The solution was washed sequentially with H$_2$O (50 mL), 1.0 N Na$_2$CO$_3$ (50 mL), and brine (50 mL), then was dried (Na$_2$SO$_4$) and concentrated. Purification by flash chroma-

Example 9

Preparation of (2R)-2-benzyl-N,4-dimethyl-N-[(1-methyl-1H-indol-2-yl)methyl]-3-oxo-2,3,4,5-tetrahydro-1H-1,4-benzodiazepine-7-carboxamide a) (2R)-2-Benzyl-N,4-dimethyl-N-[(1-methyl-1H-indol-2-yl)methyl]-3-oxo-2,3,4,5-tetrahydro-1H-1,4-benzodiazepine-7-carboxamide According to the procedure of Example 8, except using tert-butyl (2R)-2-benzyl-4-methyl-3-oxo-2,3,4,5-tetrahydro-1H-1,4-benzodiazepine-7-carboxylate (0.75 g, 2.1 mmole), 1-methyl-2-(methylaminomethyl)indole (0.34 g, 2.1 mmole), Et$_3$N (0.59 mL, 4.2 mmole), HOBt.H$_2$O (0.28 g, 2.1 mmole), and EDC.HCl (0.41 g, 2.1 mmole), the title compound (0.97 g, 100%) was prepared as an off-white solid following flash chromatography on silica gel (gradient: 80–90% EtOAc/hexanes): MS (ES) m/e 467.1 (M +H)$^+$.

Example 10

Preparation of (2R)-N,4-dimethyl-2-hydroxymethyl-N-[(1-methyl-1H-indol-2-yl)methyl]-3-oxo-2,3,4,5-tetrahydro-1H-1,4-benzodiazepine-7-carboxamide a) (2R)-N,4-Dimethyl-2-hydroxymethyl-N-[(1-methyl-1H-indol-2-yl)methyl]-3-oxo-2,3,4,5-tetrahydro-1H-1,4-benzodiazepine-7-carboxamide According to the procedure of Example 8, except using tert-butyl (2R)-2-hydroxymethyl-4-methyl-3-oxo-2,3,4,5-tetrahydro-1H-1,4-benzodiazepine-7-carboxylate (0.50 g, 1.6 mmole), 1-methyl-2-(methylaminomethyl)indole (0.26 g, 1.6 mmole), Et$_3$N (0.46 mL, 3.3 mmole), HOBt.H$_2$O (0.22 g, 1.6 mmole), and EDC.HCl (0.31 g, 1.6 mmole), the title compound (0.59 g, 91%) was prepared as an off-white solid following flash chromatography on silica gel (gradient: 2–4% MeOH/CHCl$_3$): MS (ES) m/e 407.1 (M+H)$^+$.

Example 11

Preparation of N,4-dimethyl-N-[(1-methyl-1H-indol-2-yl)methyl]-3-oxo-2,3,4,5-tetrahydro-1H-1,4-benzodiazepine-7-carboxamide a) N,4-Dimethyl-N-[(1-methyl-1H-indol-2-yl)methyl]-3-oxo-2,3,4,5-tetrahydro-1H-1,4-benzodiazepine-7-carboxamide According to the procedure of Example 8, except using tert-butyl 4-methyl-3-oxo-2,3,4,5-tetrahydro-1H-1,4-benzodiazepine-7-carboxylate (0.60 g, 2.2 mmole), 1-methyl-2-(methylaminomethyl)indole (0.35 g, 2.2 mmole), Et$_3$N (0.62 mL, 4.4 mmole), HOBt.H$_2$O (0.30 g, 2.2 mmole), and EDC.HCl (0.42 g, 2.2 mmole), the title compound (0.76 g, 92%) was prepared as an off-white solid following flash chromatography on silica gel (5% MeOH/CHCl$_3$): MS (ES) m/e 377.0 (M+H)$^+$.

Example 12

Preparation of (2R)-N,4-dimethyl-N-[(1-methyl-1H-indol-2-yl)methyl]-3-oxo-2-propyl-2,3,4,5-tetrahydro-1H-1,4-benzodiazepine-7-carboxamide a) (2R)-N,4-Dimethyl-N-[(1-methyl-1H-indol-2-yl)methyl]-3-oxo-2-propyl-2,3,4,5-tetrahydro-1H-1,4-benzodiazepine-7-carboxamide According to the procedure of Example 8, except using tert-butyl (2R)-4-methyl-3-oxo-4-propyl-2,3,4,5-tetrahydro-1H-1,4-benzodiazepine-7-carboxylate (0.60 g, 1.9 mmole), 1-methyl-2-(methylaminomethyl)indole (0.32 g, 2.0 mmole), Et$_3$N (0.56 mL, 4.0 mmole), HOBt.H$_2$O (0.27 g, 2.0 mmole), and EDC.HCl (0.39 g, 2.0 mmole), the title compound (0.40 g, 50%) was prepared as an off-white solid following flash chromatography on silica gel (EtOAc): MS (ES) m/e 419.1 (M+H)$^+$.

Example 13

Preparation of (2R)-4-benzyl-2-hydroxymethyl-N-methyl-N-[(1-methyl-1H-indol-2-yl)methyl]-3-oxo-2,3,4,5-tetrahydro-1H-1,4-benzodiazepine-7-carboxamide a) (2R)-4-Benzyl-2-hydroxymethyl-N-methyl-N-[(1-methyl-1H-indol-2-yl)methyl]-3-oxo-2,3,4,5-tetrahydro-1H-1,4-benzodiazepine-7-carboxamide According to the procedure of Example 8, except using tert-butyl (2R)-4-benzyl-2-hydroxymethyl-3-oxo-2,3,4,5-tetrahydro-1H-1,4-benzodiazepine-7-carboxylate (0.39 g, 1.0 mmole), 1-methyl-2-(methylaminomethyl)indole (0.18 g, 1.1 mmole), Et$_3$N (0.31 mL, 2.2 mmole), HOBt.H$_2$O (0.15 g, 1.1 mmole), and EDC.HCl (0.21 g, 1.1 mmole), the title compound (0.40 g, 83%) was prepared as an off-white solid following flash chromatography on silica gel (gradient: 1–3% MeOH/CHCl$_3$): MS (ES) m/e 483.2 (M+H)$^+$.

Example 14

Preparation of (2R)-2-hydroxymethyl-N-methyl-N-[(1-methyl-1H-indol-2-yl)methyl]-3-oxo-4-phenethyl-2,3,4,5-tetrahydro-1H-1,4-benzodiazepine-7-carboxamide a) (2R)-2-Hydroxymethyl-N-methyl-N-[(1-methyl-1H-indol-2-yl)methyl]-3-oxo-4-phenethyl-2,3,4,5-tetrahydro-1H-1,4-benzodiazepine-7-carboxamide According to the procedure of Example 8, except using tert-butyl (2R)-2-hydroxymethyl-3-oxo-4-phenethyl-2,3,4,5-tetrahydro-1H-1,4-benzodiazepine-7-carboxylate (0.49 g, 1.2 mmole), 1-methyl-2-(methylaminomethyl)indole (0.23 g, 1.4 mmole), Et$_3$N (0.37 mL, 2.62 mmole), HOBt.H$_2$O (0.19 g, 1.4 mmole), and EDC.HCl (0.27 g, 1.4 mmole), the title compound (0.53 g, 82%) was prepared as an off-white solid following flash chromatography on silica gel (gradient: 1–3% MeOH/CHCl$_3$): MS (ES) m/e 497.1 (M+H)$^+$.

Example 15

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 16

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 17

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound according to formula (I):

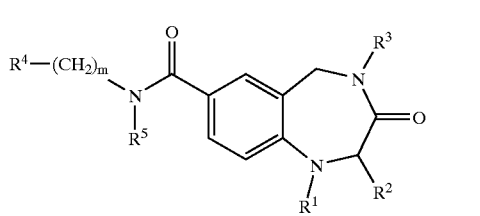

wherein:

$R^1$ is H, $C_{1-6}$alkyl or Ar—$C_{0-6}$alkyl;

$R^2$ is H, $C_{1-6}$alkyl, Ar—$C_{0-6}$alkyl, HO—$(CH_2)_n$— or R'OC(O)—$(CH_2)_n$—;

$R^3$ is A—$C_{0-4}$alkyl, A—$C_{2-4}$alkenyl, A—$C_{2-4}$alkynyl, A—$C_{3-4}$oxoalkenyl, A—$C_{3-4}$oxoalkynyl, A—$C_{1-4}$aminoalkyl, A—$C_{3-4}$aminoalkenyl, A—$C_{3-4}$aminoalkynyl, optionally substituted by any accessible combination of one or more of $R^{10}$ or $R^7$;

$R^4$ is

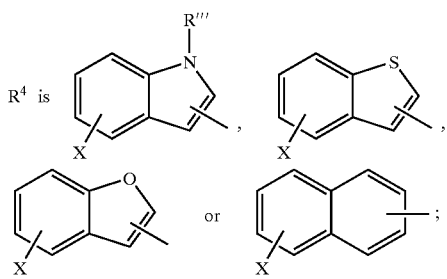

$R^5$ is H, $C_{1-6}$alkyl, Ar—$C_{0-6}$alkyl or $C_{3-6}$cycloalkyl-$C_{0-6}$alkyl;

A is H, $C_{3-6}$cycloalkyl, Het or Ar;

$R^7$ is —$COR^8$, —$COCR'_2R^9$, —$C(S)R^8$, —$S(O)_kOR'$, —$S(O)_kNR'R''$, —PO(OR'), —$PO(OR')_2$, —$B(OR')_2$, —$NO_2$, or tetrazolyl;

$R^8$ is —OR', —NR'R'', —NR'SO$_2$R', —NR'OR', or —OCR'$_2$CO(O)R';

$R^9$ is —OR', —CN, —$S(O)_rR'$, —$S(O)_kNR'_2$, —C(O)R', C(O)NR'$_2$, or —CO$_2$R';

$R^{10}$ is H, halo, —$OR^{11}$, —CN, —$NR'R^{11}$, —$NO_2$, —$CF_3$, $CF_3S(O)_r$—, —$CO_2R'$, —$CONR'_2$, A—$C_{0-6}$alkyl-, A—$C_{1-6}$oxoalkyl-, A—$C_{2-6}$alkenyl-, A—$C_{2-6}$alkynyl-, A—$C_{0-6}$alkyloxy-, A—$C_{0-6}$alkylamino- or A—$C_{0-6}$alkyl-S(O)$_r$—;

$R^{11}$ is R', —C(O)R', —C(O)NR'$_2$, —C(O)OR', —$S(O)_kR'$, or —$S(O)_kNR'_2$;

R' is H, $C_{1-6}$alkyl, Ar—$C_{0-6}$alkyl or $C_{3-6}$cycloalkyl-$C_{0-6}$alkyl;

R'' is R', —C(O)R' or —C(O)OR';

R''' is H, $C_{1-6}$alkyl, Ar—$C_{0-6}$alkyl, HO—$(CH_2)_2$—, R'C(O)—, (R')$_2$NC(O)CH$_2$— or R'S(O)$_2$—;

X is O(Ar—$C_{0-6}$alkyl), O($C_{3-6}$cycloalkyl-$C_{0-6}$alkyl), SR', $C_{1-4}$alkylsulfonyl, $C_{1-4}$alkylsulfoxyl, —CN, CH$_2$N(R')$_2$, —CO$_2$R', —CON(R')$_2$, —COR', —NR'C(O)R', or CF$_3$S(O)$_r$—;

k is 1 or 2;

m is 1, 2 or 3;

n is 1 to 6; and r is 0, 1 or 2;

or a pharmaceutically acceptable salt thereof.

2. A compound according to claim 1 in which $R^4$ is

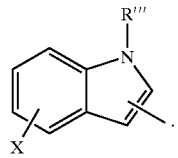

3. A compound according to claim 2 in which R''' is H, $C_{1-4}$alkyl or Ar—$C_{0-4}$alkyl.

4. A compound according to claim 1 in which $R^3$ is H, $C_{1-6}$alkyl, Ar—$C_{0-6}$alkyl, Het—$C_{0-6}$alkyl, $C_{3-6}$cycloalkyl-$C_{0-6}$alkyl, —CH$_2$CF$_3$, —(CH$_2$)$_{1-2}$C(O)OR', or —(CH$_2$)$_2$OR', wherein R' is H or $C_{1-4}$alkyl.

5. A compound according to claim 4 in which $R^3$ is H, $C_{1-4}$alkyl or Ph-$C_{0-4}$alkyl.

6. A compound according to claim 1 in which $R^1$ is H and m is 1.

7. A compound according to claim 1 in which $R^5$ is H or $C_{1-4}$alkyl.

8. A compound according to claim 1 in which $R^2$ is H, $C_{1-4}$alkyl, Ph-$C_{1-4}$alkyl, HO—(CH$_2$)$_{1-2}$— or R'OC(O)—(CH$_2$)$_{1-2}$—, wherein R' is H or $C_{1-4}$alkyl.

9. A compound which is:

(2S)-2-[(carbomethoxy)methyl]-N,4-dimethyl-N-[(1-methyl-1H-indol-2-yl)methyl]-3-oxo-2,3,4,5-tetrahydro-1H-1,4-benzodiazepine-7-carboxamide;

(2R)-2-[(carbomethoxy)methyl]-N,4-dimethyl-N-[(1-methyl-1H-indol-2-yl)methyl]-3-oxo-2,3,4,5-tetrahydro-1H-1,4-benzodiazepine-7-carboxamide;

(2R)-N-[(1-methyl-1H-indol-2-yl)methyl]-3-oxo-N,2,4-trimethyl-2,3,4,5-tetrahydro-1H-1,4-benzodiazepine-7-carboxamide;

(2R)-2-benzyl-N,4-dimethyl-N-[(1-methyl-1H-indol-2-yl)methyl]-3-oxo-2,3,4,5-tetrahydro-1H-1,4-benzodiazepine-7-carboxamide;

(2R)-2-[(carbomethoxy)methyl]-N,4-dimethyl-N-[[1-(4-hydroxybenzyl)-1H-indol-2-yl]methyl]-3-oxo-2,3,4,5-tetrahydro-1H-1,4-benzodiazepine-7-carboxamide;

(2R)-N-[[1-(4-hydroxybenzyl)-1H-indol-2-yl]methyl]-3-oxo-N,2,4-trimethyl-2,3,4,5-tetrahydro-1H-1,4-benzodiazepine-7-carboxamide;

(2R)-N,4-dimethyl-2-(hydroxymethyl)-N-[(1-methyl-1H-indol-2-yl)methyl]-3-oxo-2,3,4,5-tetrahydro-1H-1,4-benzodiazepine-7-carboxamide;

N,4-dimethyl-N-[(1-methyl-1H-indol-2-yl)methyl]-3-oxo-2,3,4,5-tetrahydro-1H-1,4-benzodiazepine-7-carboxamide;

(2R)-N,4-dimethyl-N-[[1-(4-hydroxybenzyl)-1H-indol-2-yl]methyl]-2-(hydroxymethyl)-3-oxo-2,3,4,5-tetrahydro-1H-1,4-benzodiazepine-7-carboxamide;

(2R)-N,4-dimethyl-N-[(5-benzyloxy-1-methyl-1H-indol-2-yl)methyl]-2-(hydroxymethyl)-3-oxo-2,3,4,5-tetrahydro-1H-1,4-benzodiazepine-7-carboxamide;

(2R)-N,4-dimethyl-N-2-(hydroxymethyl)-[(5-hydroxy-1-methyl-1H-indol-2-yl)methyl]-3-oxo-2,3,4,5-tetrahydro-1H-1,4-benzodiazepine-7-carboxamide;

(2R)-N,4-dimethyl-N-[(1-methyl-1H-indol-2-yl)methyl]-3-oxo-2-propyl-2,3,4,5-tetrahydro-1H-1,4-benzodiazepine-7-carboxamide;

(2R)-4-benzyl-2-(hydroxymethyl)-N-methyl-N-[(1-methyl-1H-indol-2-yl)methyl]-3-oxo-2,3,4,5-tetrahydro-1H-1,4-benzodiazepine-7-carboxamide; or (2R)-2-(hydroxymethyl)-N-methyl-N-[(1-methyl-1H-indol-2-yl)methyl-]-3-oxo-4-phenethyl-2,3,4,5-tetrahydro-1H-1,4-benzodiazepine-7-carboxamide; or a pharmaceutically acceptable salt thereof.

10. A pharmaceutical composition which comprises a compound according to any one of claims 1 to 9 and a pharmaceutically acceptable carrier.

* * * * *